Figure 1:
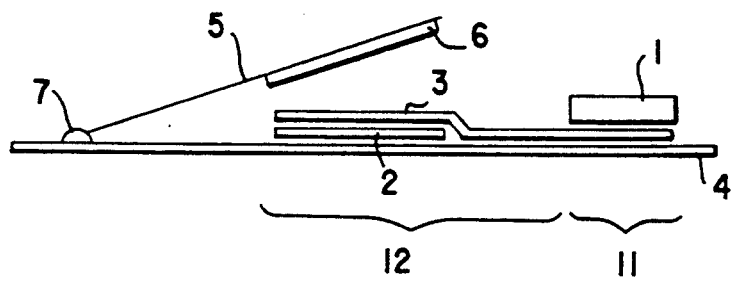

United States Patent [19]

Braun, et al

[11] Patent Number: 5,274,095
[45] Date of Patent: Dec. 28, 1993

[54] DIARYLIMIDAZOLES

[75] Inventor: Hans-Peter Braun, Weinheim, Fed. Rep. of Germany, Ulfert Deneke, Rimbach-Zolzenbach, Werner Guethein, Mannheim, Rolf Nagel, Bürstadt, all of Fed. Rep. of Germany

[73] Assignee: Boehringer Mannheim GmbH, Mannheim, Fed. Rep. of Germany

[21] Appl. No.: 928,000

[22] Filed: Aug. 11, 1992

Related U.S. Application Data

[62] Division of Ser. No. 530,661, May 30, 1990, Pat. No. 5,162,200.

[30] Foreign Application Priority Data

May 31, 1989 [DE] Fed. Rep. of Germany ....... 3917677

[51] Int. Cl.$^5$ ................. C07D 401/04; C07D 233/64; C12Q 1/50
[52] U.S. Cl. .................. 546/94; 548/335.5; 435/17; 435/28; 435/194
[58] Field of Search ........ 546/94; 548/335.5; 435/17, 28

[56] References Cited

U.S. PATENT DOCUMENTS 4,547,461 10/1985 Esders et al. .................... 435/17
4,665,023 5/1987 Deneke et al. ............. 548/315.4 X
4,788,140 11/1988 Findlay et al. .................... 435/17

FOREIGN PATENT DOCUMENTS 1175737 10/1984 Canada ............................ 435/17
122641 10/1984 European Pat. Off. .............. 435/28
56-155000 11/1981 Japan ............................ 435/17

Primary Examiner—Mary C. Lee
Assistant Examiner—Fiona T. Powers
Attorney, Agent, or Firm—Nikaido, Marmelstein, Murray & Oram

[57] ABSTRACT

Diarylimidazoles of the general formula:

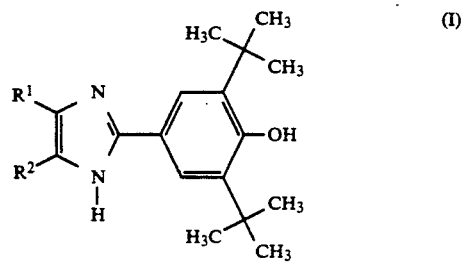

wherein $R^1$ is a radical of the general formula:

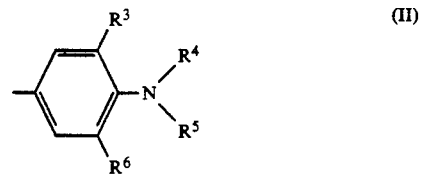

in which $R^3$ and $R^6$ are hydrogen atoms, $R^4$ and $R^5$, which can be the same or different, are lower alkyl radicals or $R^3/R^4$ and /or $R^5/R^6$ in each case together represent a lower alkylene radical and $R^2$ is a lower alkyl radical, and/or of a salt thereof, are useful as redox indicators, particularly in the presence of a SH group-containing substance.

7 Claims, 1 Drawing Sheet

DIARYLIMIDAZOLES

This is a division of application Ser. No. 530,661 filed May 30, 1990 (now U.S. Pat. No. 5,762,200).

The present invention is concerned with the use of diarylimidazoles as redox indicators, especially in the presence of one or more SH group-containing substances.

The present invention is also concerned with a process for the determination of a sample component material in which a sample is mixed with one or more SH group-containing substances and is contacted with a test system which, with the component material to be determined in the sample, forms hydrogen peroxide which is determined colorimetrically.

Furthermore, the present invention is concerned with an agent for the determination of a sample component material which contains a one or more SH group-containing substance, a test system for the detection of the sample component material by the formation of hydrogen peroxide and a redox indicator for the determination of hydrogen peroxide in the presence of peroxidase.

In addition, the present invention is concerned with diarylimidazoles of the general formula:

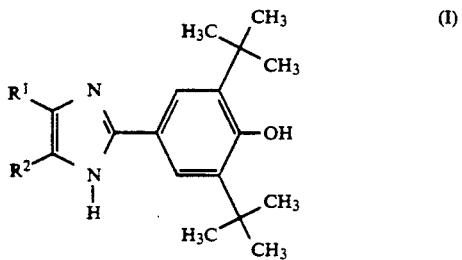

wherein $R^1$ is a radical of the general formula:

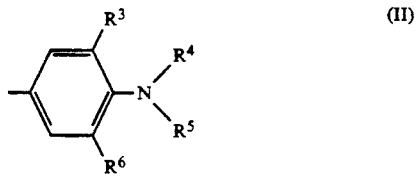

in which $R^3$ and $R^6$ are hydrogen atoms and $R^4$ and $R^5$, which can be the same or different, are lower alkyl radicals or $R^3/R^4$ and/or $R^5/R^6$ in each case together represent a lower alkylene radical and $R^2$ is a lower alkyl radical, as well as the salts thereof, with the exception of the compound 2-[3',5'-di-(tert.-butyl)-4''-hydroxyphenyl]-4(5)-(4''-dimethylaminophenyl)-5(4)-methyl-(1H)-imidazole hydrochloride, as well as with a process for the preparation of the above-mentioned diarylimidazoles.

Some enzymes possess free SH groups. If these are oxidised, the enzymatic activity decreases or the enzyme is completely inactivated. An example of such an enzyme is creatine kinase. The precise determination of the presence and amount of creatine kinase in body fluids, especially in blood serum, is of considerable importance for the prognosis of myocardial infarct and of other myopathies.

For the special case of creatine kinase, it is known that, in the case of the oxidation thereof, for example by air, free SH groups are oxidised to disulphides and the enzyme thus loses a part of its activity. Reactivation can take place by the addition of substances which contain one or more free SH groups. As such reactivating-acting SH reagents, substances are known, for example glutathione, N-acetylcysteine, dithioerythritol, dithiothreitol, mercaptoethanol and thioglucose. However, the use of such reducing-reacting compounds in detection systems with which the enzyme activity to be determined is to be determined by means of a redox indicator, i.e. of a substance which, as a result of oxidation or reduction, changes its colour, generally leads to disturbances and to false results. This is especially the case when, for a detection reaction, the enzymatic formation of hydrogen peroxide and the determination thereof by means of a redox indicator in the presence of peroxidase is to be utilised, which is very often the case. Therefore, attempts have not been lacking to make available those redox indicators and test systems which are not subject to disturbance in this regard.

From published European Patent Specification No. A-0, 116,307, an agent is known for the colorimetric determination of creatine kinase which contains triarylimidazoles according to published Federal Republic of Germany Patent Specification No. A-27 35 690. However, these imidazoles are only stable in the acidic pH range and, as experiments have shown, in the case of transfer into a weakly acidic, neutral to weakly alkaline pH range, such as is necessary in the case of many enzymatic reactions, they very easily oxidise. Furthermore, the described triarylimidazoles are so sensitive with regard to SH group-carrying substances that the concentration thereof must not exceed 0.2 mMole/liter in the test solution to be determined. However, such a low concentration of, for example N-acetylcysteine, often does not suffice for the complete reactivation of creatine kinase.

As redox indicators for the determination of hydrogen peroxide, diarylimidazoles are recommended in published European Patent Specification No. A-0,122,641. The mentioned compounds are characterised in that the aryl radical in the 2-position of the imidazole ring cannot carry any alkyl substituents and, as alkyl substituents in the 5-position of the imidazole ring, only higher alkyl homologues can be considered.

In European Patent Specification B-0,161,436, diarylimidazoles are described which are not spontaneously oxidised by atmospheric oxygen in the weakly acidic to alkaline range and which do not react with substances contained in the serum. Nothing is stated about the properties of the diarylimidazoles in the presence of SH group-carrying substances which the sample to be investigated does not originally contain. As tests have shown, the diarylimidazoles described in the two European Patent Applications as being advantageous are sensitive towards SH group-carrying substances such as are used, for example, for the reactivation of creatine kinase. A determination of creatine kinase by means of the diarylimidazoles described as being advantageous is not possible without disturbance in the presence of concentrations of SH group-carrying substances which are necessary for the complete reactivation of creatine kinase.

Therefore, it is an object of the present invention to provide redox indicators, especially for the detection of hydrogen peroxide or of peroxidate-active substances, particularly for processes and agents for the determination of sample component materials, for example creatine kinase, which do not display the above-mentioned disadvantages and which, in particular, are not influenced by SH group-carrying substances.

Surprisingly, we have found that diarylimidazoles of the general formula:

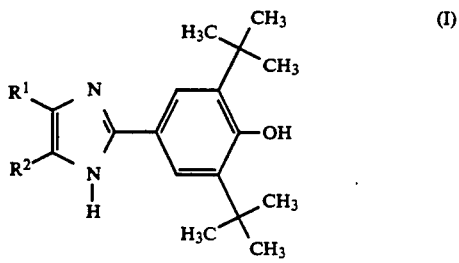

wherein $R^1$ is a radical of the general formula:

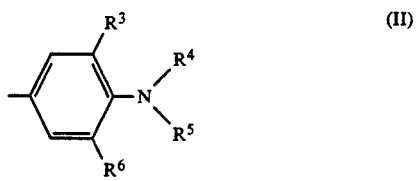

in which $R^3$ and $R^6$ are hydrogen atoms and $R^4$ and $R^5$, which can be the same or different, are lower alkyl radicals or $R^3/R^4$ and/or $R^5/R^6$ in each case together represent a lower alkylene radical and $R^2$ is a lower alkyl radical, as well as the salts thereof, satisfy the above-mentioned requirements.

Therefore, a subject of the present invention is the use of a diarylimidazole of general formula I, as described above, as a redox indicator.

In the above general formula I, lower alkyl in the definition of $R^2$, $R^4$ and $R^5$ means a radical containing up to 6 and preferably up to 4 carbon atoms, the methyl radical being especially preferred.

For the case in which $R^3/R^4$ and $R^5/R^6$ in each case together represent a lower alkylene radical, hereunder is to be understood a group containing 2 or 3 and preferably 3 carbon atoms.

Diarylimidazoles especially preferred according to the present invention are those in which $R^1$ is a p-dimethylaminophenyl radical, a p-diethylaminophenyl radical, a p-di-n-propylaminophenyl radical or a julolidine radical and $R^2$ is a methyl radical. The compound 2-[3',50'-di-(tert.-butyl)-4'-hydroxyphenyl]-4(5)-(9''-julolidyl)-5(4)-methyl-(1H)-imidazole is quite especially preferred.

Especially in solution, the diarylimidazoles of general formula I are in equilibrium with the corresponding tautomeric forms thereof of the general formula:

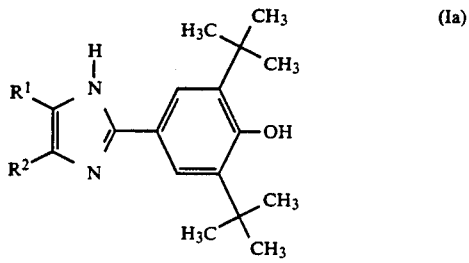

in which $R^1$ and $R^2$ have the same meanings as above. According to the present invention, the representation of general formula I is to be understood to include the corresponding tautomeric compounds. In the designation of the diarylimidazoles which are quite especially preferred according to the present invention, the bracketed expressions (4) or (5) signify the particular substituent position of the tautomeric imidazole form.

The diarylimidazoles to be used according to the present invention can be present as free bases or as salts. We have found that the salts display an even higher stability than the free bases. As salts, there are especially preferred those of strong acids, for example the hydrochlorides, sulphates and tetrafluoroborates, as well as those of aromatic sulphonic acids, for example p-toluenesulphonates and naphthalene-2-sulphonates. The hydrochlorides of the diarylimidazoles of general formula I are quite especially preferred.

The diarylimidazoles of general formula I used according to the present invention are colourless to pale beige or pale pink coloured compounds which, after oxidation, are strongly coloured.

Diarylimidazoles of general formula I are so stable that, in the weakly acidic to alkaline range, they are not spontaneously oxidised by atmospheric oxygen. Furthermore, with the compounds used according to the present invention, hydrogen peroxide and peroxidate-acting substances can also be detected in the presence of SH group-carrying substances, for example glutathione, N-acetylcysteine, dithioerythritol, dithiothreitol, mercaptoethanol and thioglucose. For example, concentrations of up to about 25 mMole/liter of N-acetylcysteine cannot disturb this detection reaction. Therefore, the diarylimidazoles of general formula I can be advantageously used in the presence of one or more SH group-containing substances as redox indicators. For this purpose, there are quite especially advantageously used those compounds described hereinbefore as being preferred.

On the basis of the above-mentioned advantageous properties, diarylimidazoles of general formula I are especially suitable for the determination of the activity of the enzyme creatine kinase which is reactivated by SH group-containing agents.

With the compounds of general formula I according to the present invention and especially with the preferred diarylimidazoles, the carrying out of a process for the determination of a sample component material is advantageously possible in which the sample is mixed with at least one SH group-containing substance and is contacted with a test system which, with the component material to be determined in the sample, forms hydrogen peroxide which, in turn, is determined colorimetrically. In such a process according to the present invention, to the sample to be investigated, for example a body fluid, especially blood, serum, plasma or urine, is added at least one SH group-containing substance in order, for example, to reactivate possible oxidised sample component materials, for example creatine kinase, in the sample. As SH group-containing substances, for this purpose there can be used, for example, glutathione, N-acetylcysteine, dithioerythritol, dithiothreitol, mercaptoethanol or thioglucose, the use of N-acetylcysteine being especially preferred.

The concentration of the SH group-containing substances possibly necessary for a dependable determination of sample component materials is dependent upon the substance to be determined and is either known to the expert or can be determined by simple experiments. In order, for example, to achieve a complete reactivation of creatine kinase in a blood sample, so much of at least one SH group-carrying substance is added thereto that the concentration in the sample to be investigated is from 2 to 20 mMole/liter. As a rule, below 2 mMole/liter, a complete enzyme activation is not possible.

The test system necessary for the determination of a sample component material depends upon the particular sample component material. The particularly appropriate test systems are known to the expert. For example, in the case of the detection process following the reactivation of creatine kinase, use is usually made of a coupling of enzymatic reactions, in which hydrogen peroxide is finally formed and is determined, from the amount thereof or the reaction per unit time can be deduced the amount of creatine kinase. A test system has proved to be useful in which, from creatine phosphate and ADP in the presence of a divalent metal cation, ATP and creatine are formed by the creatine kinase activity. ATP can then be used with a divalent metal cation and glycerokinase for the phosphorylation of glycerol. Subsequent oxidation of the glycerol-3-phosphate formed with atmospheric oxygen and glycerol-3-phosphate oxidase then leads to the formation of hydrogen peroxide.

According to the present invention, the hydrogen peroxide formed serves for an oxidation of a diarylimidazole of general formula I catalysed by peroxidase. There is hereby formed a colour absorbing in the visible wavelength range which, in principle, can be used for the determination of any sample component material, the detection of which takes place via the formation of hydrogen peroxide but which can be used especially and particularly advantageously for the quantitative determination of creatine kinase. The presence of one or more SH group-containing substances does not thereby disturb. For the process according to the present invention and especially for the determination of creatine kinase, the combination of N-acetylcysteine as SH group-carrying substance and 2-[3',5'-di-(tert.-butyl)-4'-hydroxyphenyl]-4(5)-(9''-julolidyl)-5(4)-methyl-(1H)-imidazole has proved to be especially advantageous.

The process according to the present invention can be carried out in solution, for example in a cuvette, but it can also be carried out especially advantageously in carrier-bound form.

In this case, the reagents necessary for the process according to the present invention are applied to absorbent or swellable materials such as are known to the expert as reagent carriers, for example papers, fleece, films or the like. Such reagent carriers can be used as rapid diagnostics for the direct determination of sample component materials, for example creatine kinase, in body fluids, for example blood, serum or plasma. For this purpose, the body fluid is applied directly to the reagent carrier or the reagent carrier is dipped into the body fluid. By comparison of the resultant colour with comparison colours, a semi-quantitative determination is possible. A quantitative evaluation can be carried out by means of remission photometric processes which are known to the expert.

An agent according to the present invention for the determination of a sample component material, for example creatine kinase, containing one or more SH group-carrying substances, a test system for the determination of the sample component material, for example of creatine kinase, by the formation of hydrogen peroxide and a redox indicator for the determination of hydrogen peroxide in the presence of peroxidase is characterised in that the redox indicator is a diarylimidazole of general formula I. Such an agent can be present in solution or as lyophilisate or powder mixture or pressed into a tablet for use in solution. The agent according to the present invention is especially advantageously in the form of a test carrier. In this case, the substances necessary for the determination of a sample component material, for example of creatine kinase, are present applied to solid materials. Such a test carrier can contain absorbent reagent carrier materials, for example filter papers, fleece or, for example, glass or synthetic materials or swellable or absorbent reagent films.

Figure 2:
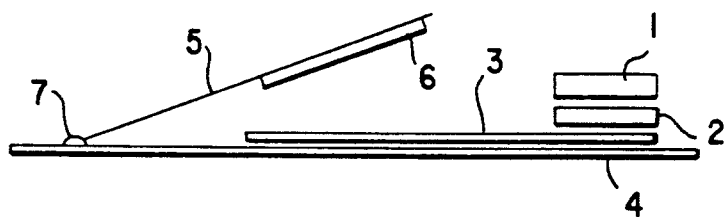
Figure 3:
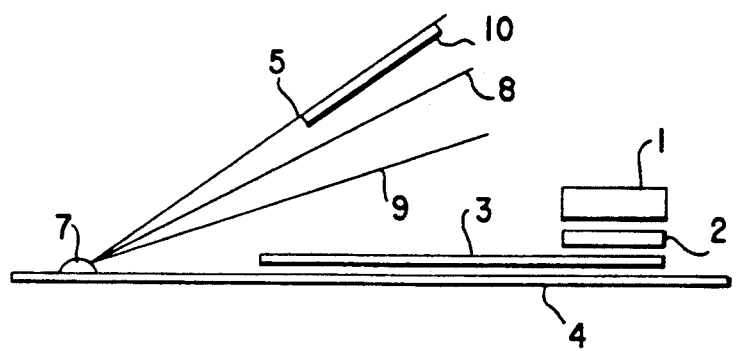

In the accompanying drawings, FIGS. 1, 2 and 3 illustrate three test carriers in cross-section which can be used for the determination of sample component materials but especially for the determination of creatine kinase in blood. They permit, on the one hand, the separation of serum or plasma from whole blood and, on the other hand, on the basis of a special construction or arrangement of the reagent and adjuvant material layers or carriers, a tempering, pre-reaction and precise start of the main reaction. The individual test carriers differ essentially only by the arrangement of the reagent carrier containing the SH group-containing substance and by the manner in which the reagents of the test system are present. More particularly, the devices are constituted as follows:

FIG. 1

On an inert carrier film (4), for example a film of synthetic material, is fixed a transport layer (3) which serves for the transport of the sample liquid from a sample application zone (11) into a detection region (12). As transport layer, in principle every material can be used which is able to transport the liquid to be investigated from the sample application zone (11) into the detection region (12) and thereby does not change it. A glass fibre fleece is especially advantageously used as transport layer. The layer (3) is partly overlapped by a layer (1) for the separation of corpuscular components from the sample liquid. In principle, for this purpose, any material can be used which permits corpuscular components to be separated from the sample liquid, especially blood cells and particularly erythrocytes from blood, and does not permit them to get into the detection region (12), where they could give rise to disturbances of the detection reaction. On the other hand, the material for the layer (1) must not so influence the sample liquid that the determination of the desired sample component material is disturbed or falsified. Glass fibre fleece, such as are described, for example, in European Patent Specification No. B-0,045,476, are especially preferred for the layer (1). In the detection region (12), between the transport layer (3) and the carrier film (4), is arranged an activation layer (2) which contains a at least one SH group-carrying substance. The activation layer (2) preferably consists of a thin absorbent material, preferably of a multifilar fabric, which is impregnated with the activating substance. Furthermore, the activating layer can also contain other substances, for example those which remove disturbing materials from the liquid to be investigated. For example, ascorbate oxidase can also be present in the activation layer for the removal of vitamin C. Laterally from the transport layer (3), a carrier film (5) consisting of transparent synthetic material is fixed via an adhesive position (7). Under the carrier film (5) is present a reagent zone (6) with the reagents necessary for the determination of the sample component material. The reagent zone (6) is so arranged that, in the case of a pressing down of the carrier film (5) in the direction of the carrier film (4), it can be brought into contact with the transport layer (3) making possible a liquid transfer. The reagent zone (6) preferably consists of a swellable and-/or absorbent film into which are incorporated the reagents necessary for the determination reaction. For the detection of creatine kinase, they can be: creatine phosphate, adenosine-5'-diphosphate (ADP), a divalent metal cation, glycerol, glycerol kinase, glycerol phosphate oxidase, peroxidase, a compound of general formula I, possibly a buffer, as well as a substance for the inhibition of serum myokinase, for example $P^1,P^5$-di-(adenosine-5') pentaphosphate. It has proved to be especially advantageous, particularly for the determination of creatine kinase from whole blood, when the activation layer (2) contains, apart from the activator substance with at least one SH group, also creatine phosphate and the reagent zone (6) the remainder of the reagents necessary for the determination.

For the determination according to the present invention of creatine kinase in blood, serum or plasma by means of diarylimidazoles of general formula I, it has proved to be quite especially advantageous when the reagent system necessary for the enzyme detection contains a detergent. Non-ionic or anionic wetting agents can preferably be used. Especially preferred are anionic wetting agents, for example dodecyl sulphate, tetradecyl sulphate and hexadecyl sulphate or the corresponding sulphonates but also, for example, diamyl sulphosuccinate. However, instead of wetting agents, there can also be used other substances which contain large-volume anions, preferably of strong acids, for example naphthalene-1,5-disulphonate, tetrafluoroborate or perchlorate, naphthalene-1,5-disulphonate being especially preferred.

Furthermore, the test system necessary for the determination of creatine kinase can also contain further materials, for example an adenylate kinase inhibitor and/or a complex former, for example ethylenediamine-tetraacetic acid (EDTA) or ethylene-glycol bis-($\beta$-aminoethyl ether)-tetraacetate (EGTA).

FIG. 2

This differs from FIG. 1 in that the activation layer (2) is placed in the sample application zone between layer (1) for the separation of corpuscular components from the sample liquid and the transport layer (3).

FIG. 3

This shows a test carrier which is constructed like the device in FIG. 2 but contains the reagents necessary for the detection of creatine kinase impregnated on different carriers (8), (9) and (10). Carrier (10) corresponds to the reagent zone (6) in FIGS. 1 and 2. The carriers (8) and (9) preferably consist of a thin, absorbent material, for example a multifilar fabric or paper.

For carrying out the process according to the present invention by means of a test carrier illustrated in the Figures, the sample to be investigated is applied as liquid to layer (1). Corpuscular components, for example erythrocytes in the case of blood, are there substantially retained. In the case of a test carrier according to FIGS. 2 and 3, the liquid passes into the activation layer (2). The sample component material, for example creatine kinase, is there reactivated by the SH group-carrying compound contained in the activation layer. The liquid with the activated material, for example creatine kinase, then subsequently fills the transport layer (3). In the case of the test carrier according to FIG. 1, the sample liquid passes through the layer (1) into the transport layer (3). It passes from there by capillary forces into the activation layer (2) positioned between the transport layer (3) and the carrier film (4) where it comes into contact with the activator substance. By means of pressing the carrier film (5) on to the layer (3), the determination reaction can be started. The liquid penetrates by means of the pressure contact into the reagent zone (6) (FIGS. 1 and 2) or into the reagent layers (8), (9) and (10) (FIG. 3). The reaction is observed, on the basis of the coloration in the reagent layers, through the carrier film (5).

The described reagent carriers provide for a pre-reaction of the serum with at least one SH group-containing compound for the reactivation of the creatine kinase, in which case the pre-reaction can also lead into the "lag phase" of the detection cascade. It is also possible that this activation and the detection of the creatine kinase take place simultaneously. For this purpose, the layer (2) can be omitted and the SH group-carrying substance placed in the reagent zone (6) (FIGS. 1 and 2) or in one of the reagent layers (8), (9) or (10) (FIG. 3).

Some typical concentrations of the reagents in the various layers of the test carriers according to FIGS. 1, 2 and 3 are:

| | |
|---|---|
| N-acetylcysteine | 0.01–0.8 $\mu$mole/cm$^2$, preferably 0.02–0.4 $\mu$mole/cm$^2$ |
| creatine phosphate | 0.2–4 $\mu$mole/cm$^2$, preferably 0.4–2.4 $\mu$mole/cm$^2$ |
| glycerol kinase | 0.1–15 U/cm$^2$, preferably 3–5 U/cm$^2$ |
| glycerol phosphate oxidase | 0.1–10 U/cm$^2$, preferably 0.6–2 U/cm$^2$ |
| horse radish peroxidase | 0.1–20 U/cm$^2$, preferably 2–10 U/cm$^2$ |
| ADP | 0.002–0.1 $\mu$mole/cm$^2$, preferably 0.007–0.05 $\mu$mole/cm$^2$ |
| glycerol | 0.01–0.5 $\mu$mole/cm$^2$, preferably 0.08–0.1 $\mu$mole/cm$^2$ |
| diarylimidazole according to the present invention | 0.01–1 $\mu$mole/cm$^2$, preferably 0.04–0.2 $\mu$mole/cm$^2$ |
| detergent | 0.01–8.0 $\mu$mole/cm$^2$, preferably 0.015–0.8 $\mu$mole/cm$^2$. |

In the carrying out of the process according to the present invention by means of test carriers according to FIGS. 1 to 3, it is ascertained that, in spite of higher concentration of SH group-carrying substance, no fading takes place of the oxidised diarylimidazole of general formula I.

Especially the process carried out with the use of test carriers provides dependable and precise results by the colour change which can be recorded in the visible wavelength between about 560 and 680 nm.

Further advantages of the process according to the present invention, especially in the case of carrying out by means of a test carrier, are that no preincubation of the sample has to take place outside of the test carrier, that especially in the case of the investigation of blood, no previous separate separation of plasma or serum is necessary, that the carrying out of the determination is possible within a very short period of time, for example for creatine kinase within 3 minutes, that also very small volumes of sample, about 30 μl., can be investigated, that in the case of the use of blood or plasma or serum, agreeing results are obtained, and that even in the presence of high concentrations of SH group-carrying substances, a stable colour development takes place.

With the exception of the compound 2-[3',5'-di-(tert.-butyl)-4'-hydroxyphenyl]-4(5)-(4''-dimethylaminophenyl)-5(4)-methyl-(1H)-imidazole hydrochloride, diarylimidazoles of the general formula:

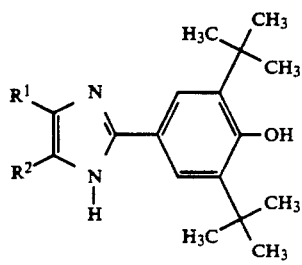

wherein $R^1$ is a radical of the general formula:

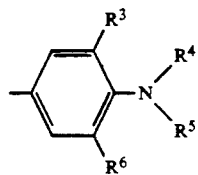

in which $R^3$ and $R^6$ are hydrogen atoms, $R^4$ and $R^5$, which can be the same or different, are lower alkyl radicals or $R^3/R^4$ and/or $R^5/R^6$ in each case together represent a lower alkylene radical and $R^2$ is a lower alkyl radical, as well as the salts thereof, are new. They are also the subject of the present invention.

The new compounds of general formula I according to the present invention can be prepared by condensing an α-diketone of the general formula:

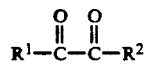

wherein $R^1$ and $R^2$ have the same meanings as in general formula I, with an aldehyde of the general formula:

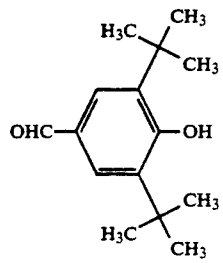

with ammonia in acid solution and subsequently possibly after-treating with an acid when a salt of a compound according to the present invention is to be obtained. The condensation reaction is preferably carried out in acetic acid solution, in which case the reaction mixture can be heated up to reflux.

The following Examples are given for the purpose of illustrating the present invention:

EXAMPLE 1

2-[3',5'-Di-(tert.-butyl)-4'-hydroxyphenyl]-4(5)-(9''-julolidinyl)-5(4)-methyl-(1H)-imidazole

1.1. Julolidine (2,3,6,7-tetrahydro-1H,5H-benzo[i, j]quinolizine)

This compound is prepared in the manner described in Organic Synthesis, III, 504.

1.2. 9-Julolidine carbaldehyde (1-(2,3,6,7-tetrahydro-1H,5H-benzo[i, j]quinolizin-9-yl)-carbaldehyde)

The synthesis of this compound is carried out analogously to P.A.S. Smith and Tung Yin Yu (J. Org. Chem., 17, 1281/1952). However, instead of N-methylformanilide, dimethylformamide is used in the case of the Vilsmeier reaction.

In a 1 liter three-necked flask equipped with a stirrer, a reflux condenser, a dropping funnel and a calcium chloride tube are placed 220 g. (1.32 mole) julolidine which is heated on a waterbath to 60° C. until it melts. It is then dissolved by the addition of 296 ml. of freshly distilled dimethylformamide and 120 ml. (about 226 g., 1.31 mole) of freshly distilled phosphoryl chloride (phosphorus oxychloride) added dropwise thereto, while stirring, over the course of 1.5 hours while cooling with ice to 20°-30° C. After subsequently stirring for 10 minutes, the reaction mixture is heated for 3 hours to 100° C. The brown, oily reaction mixture is cooled to ambient temperature and poured, while stirring, into 1.36 kg. of ice. The reaction mixture is stirred for a further hour and then placed overnight in a refrigerator. The separated crystals are filtered off with suction and washed with 100 ml. of ice water. The yellowish-green residue is subsequently dried in a vacuum to constant weight at ambient temperature over potassium hydroxide. There are obtained 255 g. (96% of theory) of the desired product; m.p. 80° C.

TLC: silica gel F 254 (E. Merck, Darmstadt, Federal Republic of Germany); elution agent: chloroform: methanol (9:1 v/v); detection: bromine vapour. $R_f$ value: 0.89.

The product is used for the next step without further purification. By recrystallisation from aqueous ethanol, a product is obtained with a melting point of 83° C.

1.3. 1-(9-Julolidyl)-propan-1-ol ([1-(2,3,6,7-tetrahydro-1H,5H-benzo[i, j]quinolizin-9-yl)-propan-1-ol])

In a 4 liter three-necked flask equipped with a stirrer, a cooler and a calcium chloride tube are placed 32.64 g. (1.34 g. atom) of magnesium turnings; these are covered with 231 ml. anhydrous diethyl ether and, without stirring, 10 ml. of a solution of 100.3 ml. (147 g. 1.34 mole) bromoethane in 100 ml. diethyl ether are added dropwise thereto. The Grignard reaction commences with gentle warming. Thereafter, while stirring, the remainder of the bromoethane solution is added thereto in such a manner that the diethyl ether keeps at the boil and the reaction mixture is then heated under reflux for a further 30 minutes. Thereafter, a solution of 135 g. (0.67 mole) of 9-julolidine carbaldehyde in 1.25 liters of tetrahydrofuran is added dropwise thereto, the speed of the dropwise addition being so adjusted that the diethyl ether keeps at the boil. Subsequently, the reaction mixture is heated under reflux for a further hour, then cooled to ambient temperature and 191 g. of ice added portionwise thereto with stirring, foaming thereby taking place. Thereafter, 382 ml. of 2N aqueous sodium hydroxide solution are added dropwise thereto, stirred for 5 minutes and left to settle. The solvent is then decanted off and the diethyl ether-tetrahydrofuran phase is dried over anhydrous sodium sulphate. After the addition of active carbon, suction filtration is carried out and the filtrate is evaporated to dryness. The oily residue is stirred with 1 liter of ligroin and, for the completion of the initiated crystallisation, left to stand overnight in a refrigerator. After filtering off with suction and washing the crystallisate with 100 ml. of cold ligroin, there are obtained, after drying for several hours in a vacuum over molecular sieve, 209 g. of beige-coloured carbinol; m.p. 74° C. A further 11.75 g. of the same product can be obtained by working up the mother liquor. Total yield 71% of theory.

TLC: silica gel F 254 (E. Merck, Darmstadt, Federal Republic of Germany); elution agent: toluene:methanol (5:1 v/v). $R_f$ value=0.3.

1.4. 1-(9-Julolidyl)-propan-1-one

[1-(2,3,6,7-tetrahydro-1H,5H-benzo[i,j]quinolizin-9-yl)-propan-1-one]

In a 6 liter three-necked flask equipped with a stirrer, a thermometer and a drying tube, 208.4 g. (0.9 mole) 1-(9-julolidyl)-propan-1-ol are dissolved in 3.4 liters acetone. 294.3 g. (1.44 mole) aluminium triisopropylate are added thereto and the reaction mixture is boiled under reflux for 4 hours with vigorous stirring and thereafter evaporated to dryness on a rotary evaporator. After the addition of 2 liters ethyl acetate and 1 liter 2N aqueous sodium hydroxide solution, the reaction mixture is vigorously stirred for 15 to 20 minutes, left to settle and decanted off from the aqueous slurry of aluminium hydroxide precipitate. The ethyl acetate phase is separated off in a separating funnel and the aqueous phase stirred up twice for 15 minutes with, in each case, 1 liter ethyl acetate. The ethyl acetate phases are combined, dried over anhydrous sodium sulphate and evaporated in a vacuum at 40° C. There are obtained 305 g. of a brown oil. This is dissolved in 500 ml. toluene-ethyl acetate (1:1 v/v), applied to a column of silica gel (Merck 60) (height 120 cm., diameter 11 cm.) and fractioned with toluene-ethyl acetate (15:1 v/v). 35 500 ml. fractions and 4 1 liter fractions are collected. Fractions 1 to 13 are discarded, fractions 14 to 33 are evaporated and fractions 34 to 39 are discarded. After evaporation of fractions 14 to 33 in a vacuum at 40° C., there are obtained 101 g. of a brown oil which is brought to crystallisation by trituration with 500 ml. ligroin. After suction filtration of the material and washing the residue with 100 ml. cold ligroin, there are obtained, after drying over phosphorus pentoxide-molecular sieve, 67 g. (31.2% of theory) of pale yellow crystals of 1-(9julolidyl)-propan-1-one; m.p. 69°-70° C.

TLC: silica gel F 254 (E. Merck, Darmstadt, Federal Republic of Germany); elution agent: toluene:methanol (5:1 v/v). $R_f$ value=0.6.

After column chromatographic separation, the mother liquid (10 g.) gives a further 2.7 g. (1.26% of theory) of pure ketone; m.p. 68°-69° C. The total yield is 33.7% of theory.

1.5. 1-(9-Julolidyl)-2-bromopropan-1-one

[2-Bromo-1-(2,3,6,7-tetrahydro-1H,5H-benzo[i,j]-quinolizin-9-yl)-propan-1-one] (M.W. 308.2)

67 g. (0.29 mole) 1-(9-julolidyl)-propan-1-one are suspended in 417 ml. of 47% hydrobromic acid and heated to 60° C., partial dissolving thereby taking place, and, within the course of 20 minutes, a solution of 15.8 ml. bromine in 87 ml. 47% hydrobromic acid is added dropwise thereto while stirring. The starting material thereby goes completely into solution. Stirring is continued for 1 hour at 60° C., cooled to 20° C. and the reaction mixture allowed to run, with intensive stirring, into a mixture of 900 ml. ethyl acetate and 1.9 liters of water. After stirring for 10 minutes, the phases are separated in a separating funnel, the aqueous phase is again shaken up twice with, in each case, 700 ml. ethyl acetate, the combined solvent extracts are dried over anhydrous sodium sulphate, filtered off with suction and evaporated on a rotary evaporator in a vacuum. The crude product obtained, 102 g. of a brown oil, is dissolved in 400 ml. of hot isopropanol and brought to crystallisation by cooling in an ice-bath. After standing for 14 hours in a refrigerator, the crystals formed are filtered off with suction and dried for 24 hours over phosphorus pentoxide to give 83.5 g. (93.4% of theory) of the yellowish-green bromoketone; m.p. 83°-84° C.

TLC: silica gel F 254 (E. Merck, Darmstadt, Federal Republic of Germany); elution agent: toluene:ethyl acetate (5:1 v/v). $R_f$ value=0.31.

1.6. 1-(9-Julolidyl)-propane-1,2-dione

[1-(2,3,6,7-tetrahydro-1H-benzo[i,j]quinolizin-9-yl)-propane-1,2-dione]

In a 1 liter three-necked flask equipped with a thermometer and a reflux condenser are placed 112 ml (1.58 mole) dimethyl sulphoxide, 46.5 g. (0.28 mole) potassium iodide and 29.7 g. (0.28 mole) anhydrous sodium carbonate. The mixture is heated with stirring to 120° C. and 86.3 g. (0.28 mole) 1-(9-julolidyl)-2-bromopropan-1-one are added thereto. The solution is stirred for 1 hour at 120° C., the yellowish solution thereby becoming red-brown. After cooling to 20° C., the reaction solution is poured into 2.8 liters of a saturated aqueous solution of sodium chloride. The resulting suspension is stirred for 15 minutes with 2 liters diethyl ether, while cooling with ice. The ethereal phase is separated off and the aqueous phase is extracted twice with, in each case, 1 liter of diethyl ether. The combined diethyl ether extracts are shaken up once with 1 liter of saturated aqueous sodium chloride solution, 1 liter of 5% aqueous sodium hydrogen carbonate solution and 1 liter of water, the ethereal phase is dried over anhydrous sodium sulphate, treated with active carbon, filtered off with suction and evaporated to dryness under a vacuum on a rotary evaporator. The crude product, 64 g. of a reddish-brown oil, is dissolved hot in 300 ml. isopropanol, cooled and brought to crystallisation by seeding and standing for 48 hours in a refrigerator: There are obtained 18.1 g. of diketone in the form of orange coloured crystals. The mother liquor is evaporated and the 30 g. of crude product obtained are purified by column chromatography. On a silica gel column (Merck 60) (height 11 cm., diameter 7.5 cm.), elution is carried out with toluene-ethyl acetate. 70 80 ml. fractions are collected.

Fractions 1 to 43 and 57 to 70 are discarded. Working up of fractions 44 to 56 give 6 g. of orange coloured oil. This is dissolved in 40 ml. of hot isopropanol, the solution is cooled and, after cooling with ice, filtered off with suction. There are obtained 5.2 g. of orange-coloured diketone. The two crystallisates are combined and again recrystallised from 150 ml. isopropanol. After filtering off with suction and washing the filter cake with a little cold isopropanol, there are obtained 22.7 g. (33.3% of theory) 1-(9-julolidyl)-propane-1,2-dione in the form of orange-coloured crystals; m.p. 111°-113° C.

TLC: silica gel F 254 (E. Merck, Darmstadt, Federal Republic of Germany); elution agent: toluene:methanol (5:1 v/v); $R_f$ value=0.32.

1.7.

2-[3',5'-di-(tert.-butyl)-4'-hydroxyphenyl]-4(5)-(9"-julolidyl)-5(4)-methyl-(1H)-imidazole

[2,6-bis-(1,1-dimethylethyl)-4-[5-methyl-4-(2,3,6,7-tetrahydro-1H,5H-benzo[i,j]quinolizin-9-yl)-imidazol-2-yl]-phenol]

In a 1 liter three-necked flask equipped with a stirrer, a cooler and a thermometer, a mixture of 32.7 g. (0.13 mole) 1-(9-julolidyl)-propane-1,2-dione, 30.5 g. (0.13 mole) 3,5-di-(tert.-butyl)-4-hydroxybenzaldehyde and 100.2 g. (1.3 mole) ammonium acetate in 300 ml. analytically pure glacial acetic acid are heated under reflux for 3 hours on an oil-bath under argon or nitrogen as protective gas atmosphere. Thereafter, the reaction mixture is cooled to 20° C. and the reaction mixture is added dropwise, with vigorous stirring, to 2 liters of ice water. After filtering off with suction the ochre-coloured residue, the filter cake is washed with 1 liter of water and the product is dried at ambient temperature for 24 hours over phosphorus pentoxide and potassium hydroxide. (All the working steps are carried out in a darkened room and with the apparatus covered with aluminum foil). The crude product, 60 g. of ochre-coloured residue, is heated under reflux with 1.8 liters acetone while stirring, the crystals obtained upon cooling are filtered off with suction, washed with 200 ml. acetone and dried for 16 hours in a vacuum over molecular sieve and phosphorus pentoxide. For the purpose of removing residual acetone, the product is stirred with 500 ml. ligroin, filtered off with suction and dried to constant weight at 40° C. with a running oil pump over molecular sieve and phosphorus pentoxide. There are obtained 31 g. (52% of theory) of pale beige-coloured crystals of 2-[3',5'-di-(tert.-butyl)-4'-hydroxyphenyl]-4(5)-(9"-julolidyl)-5(4)-methyl-(1H)-imidazole; m.p.>260° C. (decomposition from 300° C.).

TLC: finished plate silica gel F 254 (E. Merck, Darmstadt, Federal Republic of Germany); elution agent: dioxan/acetic acid/toluene (20:80:72 v/v/v); $R_f$ value=0.35. Detection: chlorine/tetramethylbenzidinepotassium iodide.

EXAMPLE 2

2-[3',5'-di-(tert.-butyl)-4'-hydroxyphenyl]-4(5)-(9"-julolidyl)-5(4)-methyl-(1H)-imidazole hydrochloride

[2,6-bis-(1,1-dimethylethyl)-4-[5-methyl-4-(2,3,6,7-tetrahydro-1H,5H-benzo[i,j]quinolizin-9-yl)imidazol-2-yl]-phenol hydrochloride 20 g. (0.437 mole) of the imidazole obtained in Example 1 are suspended in 50 ml. methanol and, while cooling to ambient temperature, 30 ml. saturated ethereal hydrochloric acid are added dropwise thereto, the base thereby going into solution. Thereafter, it is evaporated at ambient temperature in a vacuum and the oily residue is triturated with 200 ml. ethyl acetate. After placing for 15 minutes in an ice-bath, the crystals formed are sharply filtered off with suction, washed with a little ice-cold ethyl acetate and dried to constant weight in a vacuum at ambient temperature over phosphorus pentoxide. There are obtained 19.8 g. (87.1% of theory) of pink-coloured crystals; m.p. 231° C. (decomp.).

$R_f$ value in the elution agent toluene:dioxan:glacial acetic acid (9:2.5:1 v/v/v), silica gel 60 (E. Merck, Darmstadt, Federal Republic of Germany)=0,38.

EXAMPLE 3 a)

2-[3',5'-di-(tert.-butyl)-4'-hydroxyphenyl]-4(5)-(4"-diethylaminophenyl)-5(4)-methyl-(1H)-imidazole hydrochloride 0.05 mole 1-(4'-N-diethylaminophenyl)-propane-1,2-dione (respectively 1-[4-(diethylamino)phenyl]-propane-1,2-dione) (obtained analogously to 1-(9-julolidyl)-propane-1,2-dione from Example 1 as oil; TLC: silica gel 60 (E. Merck, Darmstadt, Federal Republic of Germany), elution agent: toluene/ethyl acetate 4:1 (v/v), $R_f$ value=0.8) are heated under reflux for 4 hours with 11.72 g. (0.05 mole) 3,5-di-(tert.-butyl)-4-hydroxybenzaldehyde and 38.5 g. (0.5 mole) ammonium acetate in 100 ml. glacial acetic acid under argon as protective gas. After standing for 12 hours at ambient temperature, the dark coloured reaction mixture is poured on to 550 g. of ice and 50 ml. of concentrated aqueous ammonia solution, the precipitate formed is sharply filtered off with suction and the crude product is taken up in ethyl acetate. After drying and evaporation, the product is converted into the hydrochloride by dissolving in methanol and adding ethereal hydrochloric acid. After recrystallisation from isopropanol, there is obtained the stable end product in a yield of 40% of theory; m.p. 220° C. (decomp.).

$\lambda_{max}$ 672 nm ($\epsilon$=21,758)

TLC: silica gel 60 (E. Merck, Darmstadt, Federal Republic of Germany); elution agent: toluene/methanol 5:1 v/v; $R_f$=0.33.

Intermediate compounds necessary for production of the diketone:

1-[4-(diethylamino)phenyl]-propane-1-one (4'-N-diethylamino)propiophenone) obtained according to GB-A-911,342 (Wellcome), analogous to A. W. Nineham, Soc. 635 (1952): b.p. 135°-155° C., m.p. 44°-45° C., yield of 55% of theory—TLC: silica gel 60 (E. Merck, Darmstadt, Federal Republic of Germany); elution agent: toluene/ethyl acetate 4:1 v/v, $R_f$=0.6.

1-[4-(Diethylamino)phenyl]-2-bromopropane-1-one: yield of 98% of theory, m.p. 59°-61° C.; TLC: silica gel 60 (E. Merck, Darmstadt, Federal Republic of Germany), elution agent: toluene/ethyl acetate 4:1 v/v, $R_f$=0.7.

b)

2-[3',5'-Di-(tert.-butyl)-4'-hydroxyphenyl)-4(5)-(4"'-N-di-n-propylaminophenyl)-5(4)-methyl-(1H)-imidazole hydrochloride Analogously to Example 3a), this compound is prepared from 1-(4'-di-n-propylaminophenyl)-propane-1,2-dione (respectively 1-(4-di-n-propylaminophenyl)-propane-1,2-dione) (obtained analogously to 1-(9'-julolidyl)-propane-1,2-dione from Example 1 as an oil, TLC silica gel 60 (E. Merck, Darmstadt, Federal Republic of Germany), elution agent: methylene chloride, $R_f=0.4$) as base with a melting point of 33°–34° C. (after recrystallisation from n-heptane); TLC: silica gel 60 (E. Merck, Darmstadt, Federal Republic of Germany); elution agent: methylene chloride, $R_f$ value=0.2. The yield is 40% of theory. Analogous to Example 3 the hydrochloride is obtained from the base: m.p. 246°–248° C.

$\lambda_{max}=667$ nm ($\epsilon=20.700$)

TLC: silica gel 60 (E. Merck, Darmstadt, Federal Republic of Germany); elution agent: toluene/methanol 5:1 v/v, $R_f$ value=0.38.

Intermediate compounds necessary for the production of the diketone:

4-Dipropylaminobenzaldehyde, prepared from N,N-dipropylaniline according to Duff. Furness, Soc. 1952, 1162: b.p. (0.1 torr) 145°–148° C., TLC: silica gel 60 (E. Merck, Darmstadt, Federal Republic of Germany), elution agent: n-heptane/methylethylketone 2:1 v/v, $R_f=0.57$.

1-[4-(Di-n-propylamino)phenyl]-propane-1-ol: yield of 90% of theory, oil. TLC: silica gel 60 (E. Merck, Darmstadt, Federal Republic of Germany), elution agent: toluene/ethyl acetate 4:1 v/v, $R_f=0.46$.

1-[4-(Di-n-propylamino)phenyl]-propane-1-one: yield of 48% of theory, m.p. 41°–43° C., TLC: silica gel 60 (E. Merck, Darmstadt, Federal Republic of Germany), elution agent: toluene/ethyl acetate 4:1 v/v, $R_f=0.7$.

1-[4-(Di-n-propylamino)phenyl]-2-bromopropane-1-ol: yield of 87% of theory, yellow oil. TLC: silica gel 60 (E. Merck, Darmstadt, Federal Republic of Germany), elution agent: toluene/ethyl acetate 4:1 v/v, $R_f=0.8$.

c) Instead of the direct conversion of the 1-[4-dialkylamino)phenyl]-2-bromopropane-1-ones to the corresponding 1-[4-(dialkylamino)phenyl]-propane-1,2-diones it is possible to choose the way via the corresponding 2-acetoxy-respectively 2-hydroxy compounds with following oxidation by copper salts, especially copper acetate. The method will be explained by a general example in the following:

Conversion of 1-[4-(dialkylamino)phenyl]-2-bromopropane-1-ones to 1-[4-(dialkylamino)phenyl]-propane-1,2-diones 0.1 mole 1-[4-(dialkylamino)phenyl]-2-bromopropane-1-one in 170 ml. glacial acetic acid with 0.8 mole anhydrous sodium acetate are stirred 3 hours at 130° C. Thereafter, water is added up to 900 ml. and the obtained oil is separated by shaking out with 3×200 ml. methylene chloride. After washing the organic phase with water and evaporation in a vacuum the respective acetoxy compound is obtained in a nearly quantitative yield.

This crude product is stirred with 88 ml. 2N hydrochloric acid for 2 hours at 80° C. After cooling the reaction mixture is neutralized by careful adding of 30 g. sodium hydrocarbonate and the obtained 1-[4-(dialkylamino)phenyl]-2-hydroxy-propane-1-one is shaken out with 3×100 ml. methylene chloride. The combined organic phases are shaken with 200 ml. water, dried and evaporated. The yield is quantitative. The obtained product is stirred with 51 g. (0.25 mole) copper (II) acetate H$_2$O, 200 ml. ethanol and 100 ml. water for 6.5 hours at 90° C. After suction filtration of the precipitate the residue is washed with a little ethanol/water 2:1 v/v. The filtrate is diluted with 500 ml. water and the separated oil is shaken out with 3×200 ml. methylene chloride. After washing the combined organic phases with water, drying and evaporation, the residue is chromatographed on a silica gel column (600 g. silica gel 60 (E. Merck, Darmstadt, Federal Republic of Germany), diameter 7.5 cm, height 45 cm) carried out with methylene chloride.

The respective intermediate compounds are:

aa) 1-[4-(Diethylamino)phenyl]-2-acetoxypropane-1-one: yield of 90% of theory, m.p. 75°–77° C., TLC: silica gel 60 (E. Merck, Darmstadt, Federal Republic of Germany), elution agent: toluene/ethyl acetate 4:1 v/v, $R_f=0.5$.

1-[4-(Diethylamino)phenyl]-2-hydroxypropane-1-one: yield of 79.5% of theory, amorphous, TLC: silica gel 60 (E. Merck, Darmstadt, Federal Republic of Germany), elution agent: toluene/ethyl acetate 4:1 v/v, $R_f=0.4$.

bb) 1-[4-(Di-n-propylamino)phenyl]-2-acetoxypropane-1-one: yield of 92.2% of theory, brown oil, TLC: silica gel 60 (E. Merck, Darmstadt, Federal Republic of Germany), elution agent: toluene/ethyl acetate 4:1 v/v, $R_f=0.5$.

1-[4-(Di-n-propylamino)phenyl]-2-hydroxypropane-1-one: yield of 98.9% of theory, oil, TLC: silica gel 60 (E. Merck, Darmstadt, Federal Republic of Germany), elution agent: toluene/ethyl acetate 4:1 v/v, $R_f=0.42$.

EXAMPLE 4

Test Carrier for the Determination of Creatine Kinase

A test carrier is produced according to FIG. 1 of the accompanying drawings. Layer (1) is a 0.5 mm. thick glass fibre fleece made of glass of the quality 753 Type 108A (Johns Mansville, U.S.A.) with a weight per unit surface area of 50–60 g./m$^2$ and a size of 6 mm.×6 mm.

The transport layer (3) is a 0.15 mm. thick glass fibre fleece made of glass of the quality 753 Type 106 (Johns Mansville, U.S.A.), reinforced with 10% polyester fibres, a weight per unit surface area of 20–25 g./m$^2$ and a size of 16 mm.×6 mm.

The activating layer (2) consists of a polyester fabric 14/100 of the firm SST/Switzerland with an absorption capacity of about 55 ml./m$^2$ and an air permeability of about 5000 l./m$^2$ sec. This material is impregnated with an aqueous solution, adjusted to pH 8.0, containing 200 mMole/liter creatine phosphate, 30 mMole/liter N-acetylcysteine and 0.05% by weight of Triton X-100. The fabric has the dimensions 12 mm.×6 mm.

The carrier film (5) is transparent and consists of polycarbonate. It is 15 mm. long and 6 mm. wide.

The reagent zone (6) is produced by mixing Propiofan (BASF, Ludwigshafen, Federal Republic of Germany), kieselguhr (grain size distribution 100% <48 μm., 95%≦32 μm., 70%≦16 μm., 25–45%<8 μm. (Eagle Picker, U.S.A.), titanium dioxide Type P-25 highly dispersed (Degussa, Federal Republic of Germany) and xanthene (Kelco Oil International, Hamburg, Federal Republic of Germany) in a weight ratio of 1:2:0.8:0.04 and worked up to give a viscous mass. In an amount of phosphate buffer (pH 7.3) which is double the amount of kieselguhr, there are dissolved:

| | |
|---|---|
| ascorbate oxidase | 200 U/g. |
| glycerol kinase | 300 U/g. |
| α-glycerol phosphate oxidase | 50 U/g. |
| horse radish peroxidase | 60 U/g. |
| glycerol | 8 μmole/g. |

-continued

| | |
|---|---|
| magnesium aspartate | 10 μmole/g. |
| adenosine diphosphate | 30 μmole/g. |
| adenosine monophosphate | 2 μmole/g. |
| P¹, P⁵-di-(adenosine-5')-pentaphosphate | 2.7 nmole/g. |
| sodium dodecyl sulphate | 8 μmole/g. |
| Triton X-100 | 2% by wt. |
| 2-[3',5'-di-(tert.-butyl)-4'-hydroxyphenyl]-4(5)-(9"-julolidyl)-5(4)-methyl-(1H)-imidazole hydrochloride | 40 μmole/g. |

The viscous mass and the phosphate buffer solution are worked up to give a flowable mass and applied in a rake coating process in a layer thickness of 200 μ to a polycarbonate film.

The individual layers are fixed by means of a melt adhesive to the carrier film (4) as shown in FIG. 1 of the accompanying drawings.

For the determination of creatine kinase in blood, 30 μl. of blood, plasma or serum are applied to the separation layer (1). After 60 seconds, the carrier film (5) with the reagent zone (6) is pressed on to transport layer (3) and the colour change in the reagent zone (6) measured reflection photometrically in the next 2 minutes. The creatine kinase activity to be determined can be read off by means of the measured reflection values from a calibration curve.

As can be seen from the following Table 1, for blood samples of differing haematocrits but with the same creatine kinase content, there can be obtained results for the creatine kinase activity which agree well.

TABLE 1

| haematocrit in % | creatine kinase activity in U/l. |
|---|---|
| 20 | 71 |
| 30 | 74.5 |
| 40 | 73.5 |
| 44 | 73.5 |
| 50 | 71 |

From the following Table 2, it can be seen that, in the case of samples from the same donor, within the limits of measurement error exactitude, agreeing results can also be obtained from plasma and whole blood. In each case, the haematocrit was 44%.

TABLE 2

| donor | creatine kinase activity in U/l. | |
|---|---|---|
| | blood | plasma |
| 1 | 73.5 | 72 |
| 2 | 745 | 740 |
| 3 | 1610 | 1625 |

It is to be observed that, in the case of the use of the same volume of plasma and blood, on the basis of the haematocrit with the blood sample on the test carrier an up to 4 times higher N-acetylcysteine concentration is adjusted as with plasma. Thus, the results of Table 2 demonstrate that, even in the case of increased concentration of SH group-containing substance in the sample liquid, dependable results are obtained. The same conclusion is to be drawn from the results of the following Table 3 in which different sample volumes (serum) were applied to the test carrier and the creatine kinase activity was measured.

TABLE 3

| sample volume | creatine kinase activity in U/l. in serum | |
|---|---|---|
| μl. | donor 1 | donor 2 |
| 28 | 92 | 2127 |
| 30 | 92 | 2122 |
| 32 | 96 | 2216 |
| 35 | 94 | 2248 |

The results show that the test carrier according to the present invention for the determination of creatine kinase is volume-independent over a wide range and not only in the case of low but also in the case of high N-acetylcysteine concentrations provides agreeing results.

EXAMPLE 5

Comparison of Diarylimidazoles in Test Carriers According to FIG. 1

A) Test carriers are produced in the manner described in Example 4. They differ from one another only with regard to the diarylimidazole used.

Test carrier 1 contains 2-(3',5'-dimethoxy-4'-hydroxyphenyl)-4(5)-(4"-dimethylaminophenyl)-5(4)-methyl-(1H)-imidazole hydrochloride.

Test carrier 2 contains 2-[3',5'-di-(tert.-butyl)-4'-hydroxyphenyl]-4(5)-(4"-dimethylaminophenyl)-5(4)-methyl-(1H)-imidazole hydrochloride.

Test carrier 3 contains 2-[3',5'-di-(tert.-butyl)-4'-hydroxyphenyl]-4(5)-(4"-diethylaminophenyl)-5(4)-methyl-(1H)-imidazole hydrochloride.

Test carrier 4 contains 2-[3',5'-di-(tert.-butyl)-4'-hydroxyphenyl]-4(5)-(4"-di-n-propylaminophenyl)-5(4)-methyl-(1H)-imidazole hydrochloride.

Test carrier 5 contains 2-[3',5'-di-(tert.-butyl)-4'-hydroxyphenyl]-4(5)-(4"-aminophenyl)-5(4)-methyl-(1H)-imidazole hydrochloride.

Test carrier 6 is identical with the test carrier according to the present invention produced in Example 4.

In the case of the use of, in each case, 30 μl. of serum, there are obtained the results given in the following Table 4.

TABLE 4

| test carrier No. | creatine kinase activity in U/l. |
|---|---|
| 1 | less than 0.1 |
| 2 | 2061 |
| 3 | 2043 |
| 4 | 2087 |
| 5 | 430 |
| 6 | 2100 |

From the above-given results, it is clear that only the diarylimidazoles according to the present invention in test carriers 2, 3, 4 and 6 can be used without the oxidation product of the indicator formed being bleached by N-acetylcysteine (as in the case of carriers 1 and 5).

B) Test carriers are produced as described in A) above, none of which contain N-acetylcysteine. In the case of the use of, in each case, 30 μl. of serum, there are obtained the results given in the following Table 5.

TABLE 5

| test carrier No. | creatine kinase activity in U/l. |
|---|---|
| 1 | 1071 |
| 2 | 1100 |
| 3 | 980 |
| 4 | 1020 |

TABLE 5-continued

| test carrier No. | creatine kinase activity in U/l. |
| --- | --- |
| 5 | 957 |
| 6 | 1032 |

Without N-acetylcysteine, no reactivation of oxidised creatine kinase takes place. Test carriers 1 to 6 provide comparable results which, however, are all lower in their values than those given in the above Table 4.

In the case of comparison with the results given in Table 4, it is to be ascertained that the diarylimidazoles of test carriers 1 and 5 are clearly disturbed by N-acetylcysteine. On the other hand, the diarylimidazoles according to the present invention in test carriers 2, 3, 4 and 6 are very well suited for measurements in the presence of N-acetylcysteine.

What is claimed is:

1. A diarylimidazole compound of the formula

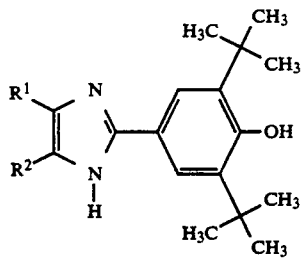

or a tautomer thereof, wherein $R^2$ is lower alkyl and $R^1$ is 9-julolidyl or a salt thereof.

2. 2-[3',5'-di-(tert.-butyl)-4'-hydroxyphenyl]-4(5)-(9''-julolidyl)-5(4)-methyl-(1H)-imidazole or a salt thereof.

3. A reagent for the colorimetric determination of a peroxidate-acting substance in a sample inclusive of a sulfhydryl-containing substance, which comprises a compound of claim 1 and a peroxidase.

4. A reagent for the colorimetric determination of a peroxidate-acting substance in a sample inclusive of a sulfhydryl-containing substance, which comprises 2-[3',5'-di-(tert.-butyl)-4'-hydroxyphenyl]-4(5)-(9''-julolidyl)-5(4)-methyl-(1H)-imidazole or a salt thereof, and a peroxidase.

5. A reagent according to claim 3, wherein the peroxidate-active substance is used determine creatine kinase.

6. A reagent according to claim 5, wherein the sulfhydryl-containing substance is glutathione, N-acetylcysteine, dithioerythritol, dithiothrietol, mercaptoethanol or thioglucose.

7. A reagent according to claim 6 wherein the compound of claim 1 is 2-[3',5'-di-(tert.-butyl)-4'-hydroxyphenyl]-4(5)-(9''-julolidyl)-5(4)-methyl-(1H)-imidazole or a salt thereof.

* * * * *